(12) United States Patent
Kang

(10) Patent No.: US 6,810,923 B2
(45) Date of Patent: Nov. 2, 2004

(54) PIPET FOR LIQUID EXCHANGE

(75) Inventor: Jing X. Kang, North Andover, MA (US)

(73) Assignee: Biodevices, Inc., Woburn, MA (US)

(*) Notice: Subject to any disclaimer, the term of this patent is extended or adjusted under 35 U.S.C. 154(b) by 0 days.

(21) Appl. No.: 10/169,636

(22) PCT Filed: Jan. 2, 2001

(86) PCT No.: PCT/US01/00139
§ 371 (c)(1),
(2), (4) Date: Nov. 25, 2002

(87) PCT Pub. No.: WO01/49415
PCT Pub. Date: May 12, 2001

(65) Prior Publication Data
US 2003/0205289 A1 Nov. 6, 2003

Related U.S. Application Data

(60) Provisional application No. 60/250,285, filed on Nov. 30, 2000, and provisional application No. 60/174,490, filed on Jan. 4, 2000.

(51) Int. Cl.[7] .................................................. B01L 3/02
(52) U.S. Cl. .................. 141/65; 422/100; 604/902; 73/864.12; 73/864.15
(58) Field of Search ........................... 141/65; 422/100; 604/35, 902; 73/864.11, 864.12, 864.15

(56) References Cited

U.S. PATENT DOCUMENTS

| | | | | |
|---|---|---|---|---|
| 3,955,930 A | * | 5/1976 | Shapiro | 422/50 |
| 4,516,398 A | * | 5/1985 | Wuchinich | 604/22 |
| 4,635,665 A | * | 1/1987 | Namba et al. | 134/167 R |
| 5,084,241 A | * | 1/1992 | Parker | 422/100 |
| 5,158,748 A | * | 10/1992 | Obi et al. | 422/100 |
| 5,542,918 A | * | 8/1996 | Atkinson | 604/27 |
| 5,827,218 A | * | 10/1998 | Nguyen et al. | 604/30 |
| 5,840,253 A | * | 11/1998 | Chase et al. | 422/63 |
| 5,853,665 A | * | 12/1998 | Ade et al. | 422/62 |
| 5,874,296 A | * | 2/1999 | Kang | 435/283.1 |
| 5,895,762 A | * | 4/1999 | Greenfield et al. | 436/43 |

FOREIGN PATENT DOCUMENTS

DE    4321062 A1 * 5/1995    ............ C12M/3/00

* cited by examiner

Primary Examiner—J. Casimer Jacyna
(74) Attorney, Agent, or Firm—Fish & Richardson P.C.

(57) ABSTRACT

The invention features pipets for fast and efficient liquid exchange, pipet controllers for use with such pipets, and pipetting systems utilizing pipets and/or pipet controllers of the invention.

14 Claims, 11 Drawing Sheets

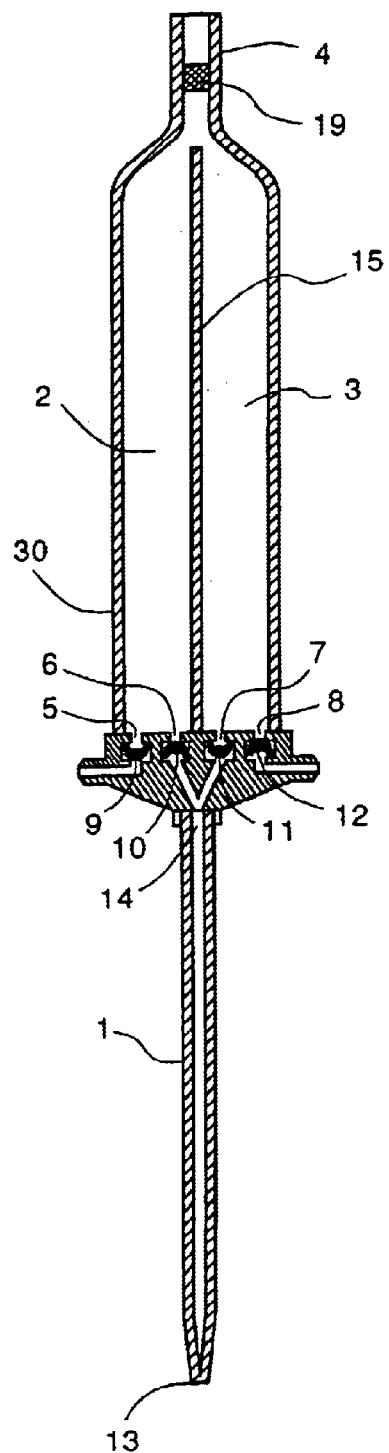
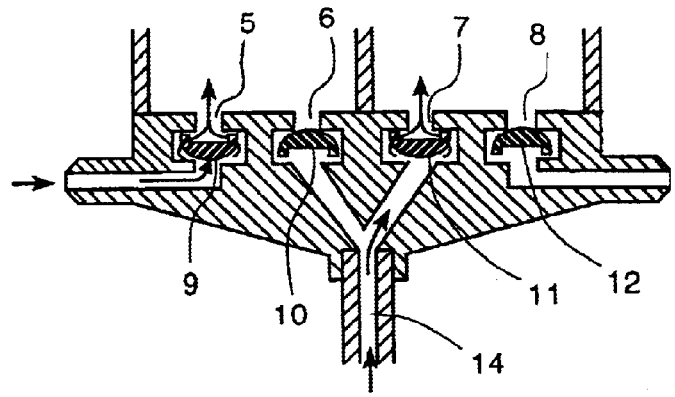
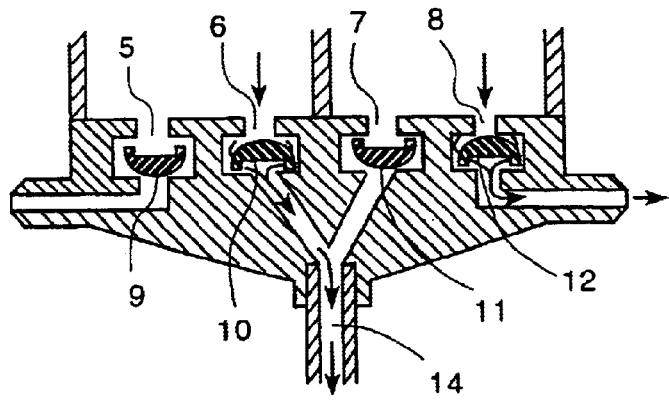

FIG. 3A
FIG. 3B
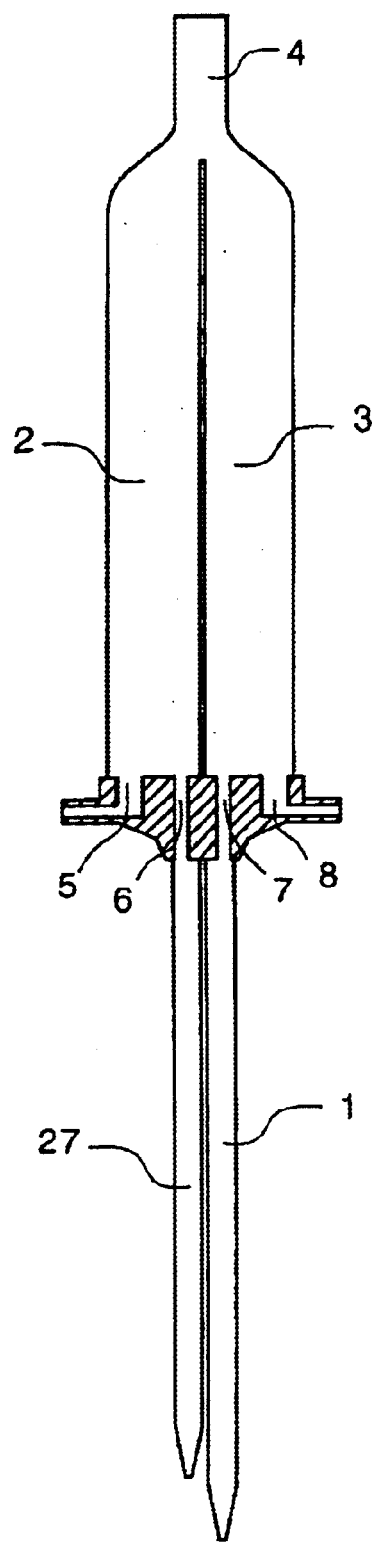
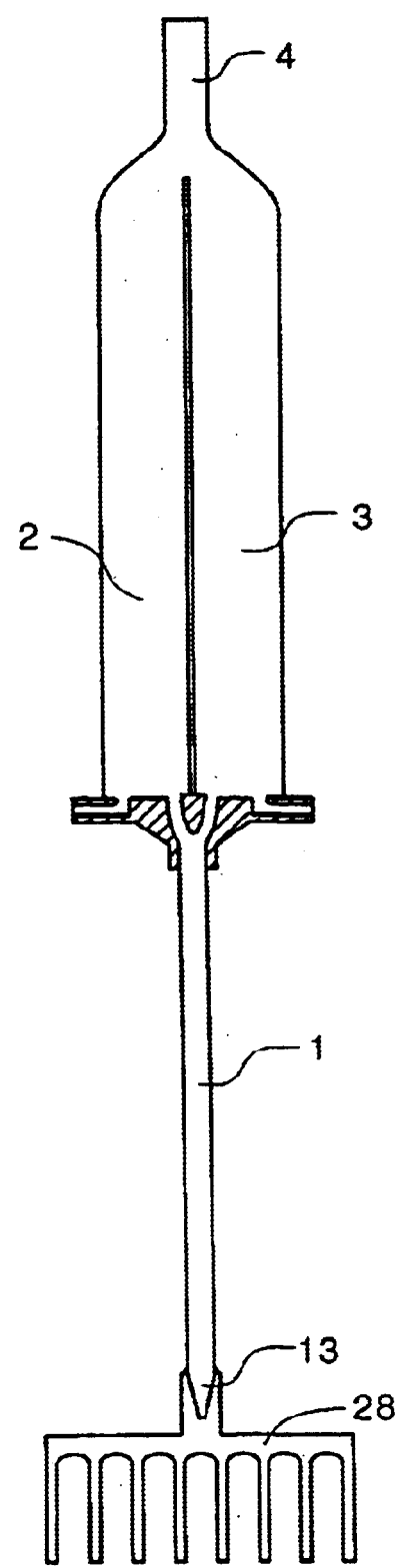

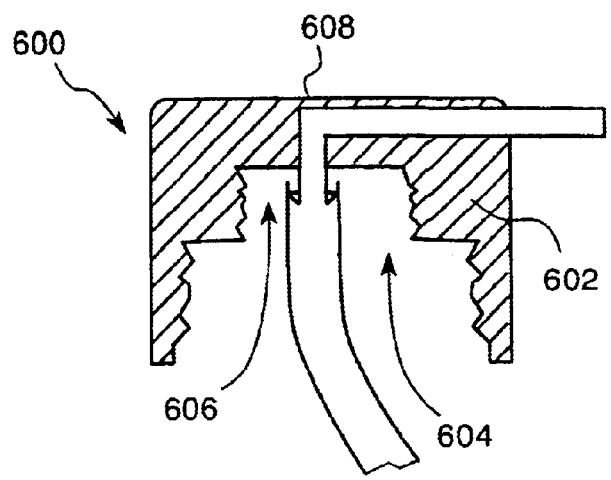
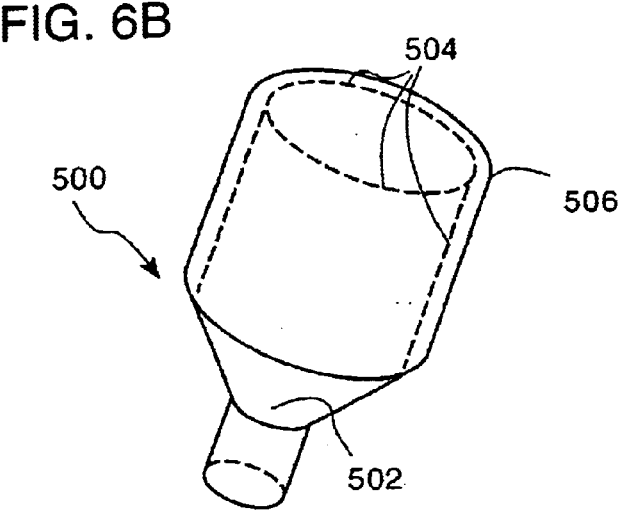
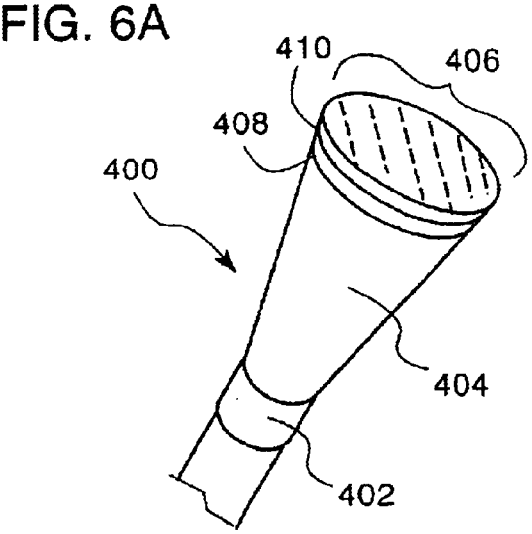

PIPET FOR LIQUID EXCHANGE

CROSS-REFERENCE TO RELATED APPLICATIONS

This application claims priority from U.S. Provisional Application Ser. No. 60/250,285, filed Nov. 30, 2000; and U.S. Provisional Application Ser. No. 60/174,490, filed Jan. 4, 2000.

BACKGROUND OF THE INVENTION

The present invention relates to laboratory pipets for changing liquid residing in a vessel, e.g., a tissue culture vessel. Changing liquid medium is routine (often called cell feeding) in laboratories that use cell/tissue cultures and is generally performed every other day. The conventional operation of cell feeding typically involves at least two separate steps: 1) removal or aspiration of the old medium from a culture vessel by means of vacuum suction or pipetting; and 2) addition of new medium to the culture vessel using another pipet to transfer medium from a liquid container to the culture vessel.

Conventional laboratory pipets, which are usually used with an electrical/mechanical pipetter for drawing and expelling fluids, have a single barrel and therefore can handle (take and discharge) only one liquid at a time. This process requires a change of pipets, thereby rendering the process discontinuous and requiring many actions, pauses, openings of culture vessels and medium containers, and seconds or minutes of prolonged exposure of cultured cells to air. Consequently, cell feeding is time consuming, material-wasting, and potentially harmful to cultured cells, particularly when a large volume of medium or a large number of vessels are involved.

To solve the aforementioned problems, a method and apparatus for a one-step liquid medium exchange is described in U.S. Pat. No. 5,874,296, which is hereby incorporated by reference. The apparatus comprises a vacuum controller, a pipe, and a reservoir. The apparatus is capable of suctioning a liquid (old medium) from a container using a vacuum and simultaneously drawing a second liquid (new medium) from a liquid source to fill the reservoir. When the old medium is completely extracted and sufficient new medium fills the reservoir, the vacuum controller disengages the vacuum to stop fluid transfer. Activation of another controller allows the new medium to drain from the reservoir into the now empty container which formerly contained the old medium. Use of this apparatus can now accomplish the task of changing liquid media in essentially one step. An installed vacuum source is generally required for operation of the apparatus.

SUMMARY OF THE INVENTION

The present invention is based on a variety of new features that increase the flexibility and efficiency of the one-step liquid medium exchange system described in U.S. Pat. No. 5,874,296. In one embodiment, a pipet includes a first reservoir for holding the liquid to be freshly added to a vessel, and a second reservoir for holding the waste liquid removed from the vessel. Visual inspection of the fluid levels in the first and second reservoirs helps the user confirm both the volume of liquid removed from the vessel and the volume of liquid to be introduced into the vessel. In another embodiment, a pipet controller includes a conduit and valve control system for controlling liquid flow through the controller, in contrast to previously available pipet controllers that do not allow liquid to flow through the controller.

Accordingly, the invention features a pipet having (1) a delivery reservoir including an inlet port that allows passage of liquid into but not out of the delivery reservoir, the inlet port adapted for attachment to a liquid source, and an outlet-port that allows passage of liquid out of but not into the delivery reservoir, the delivery reservoir formed of a material substantially transparent to allow visual inspection of liquid level within the delivery reservoir; (2) a disposal reservoir including an inlet port that allows passage of liquid into but not out of the disposal reservoir, and an outlet port that allows passage of liquid out of but not into the disposal reservoir, the outlet port adapted for attachment to a waste receptacle, and the disposal reservoir formed of a material substantially transparent to allow visual inspection of liquid level within the disposal reservoir, (3) a tube having a distal end and proximal end, the distal end adapted for suction of liquid from and delivery of liquid to a vessel, and the proximal end in communication with the outlet port of the delivery reservoir and the inlet port of the disposal reservoir, and (4) a vacuum port contiguous with the delivery reservoir and the disposal reservoir and adapted for attachment to a vacuum source.

In an alternative embodiment, the invention includes a pipet having (1) a delivery reservoir including an inlet port that allows passage of liquid into but not out of the delivery reservoir, the inlet port adapted for attachment to a liquid source, and an outlet port that allows passage of liquid out of but not into the delivery reservoir, the delivery reservoir formed of a material substantially transparent to allow visual inspection of liquid level within the delivery reservoir, (2) a disposal reservoir including
an inlet port that allows passage of liquid into but not out of the disposal reservoir, and
an outlet port that allows passage of liquid out of but not into the disposal reservoir, the outlet port adapted for attachment to a waste receptacle, and the disposal reservoir formed of a material substantially transparent to allow visual inspection of liquid level within the disposal reservoir; (3) a suction tube having a distal end adapted for suction of liquid from a vessel and a proximal end in communication with the inlet port of the disposal reservoir; (4) a delivery tube having a distal end adapted for delivery of liquid from a vessel and a proximal end in communication with the outlet port of the delivery reservoir; and (5) a vacuum port contiguous with the delivery reservoir and the disposal reservoir and adapted for attachment to a vacuum source, Application of a vacuum to the pipets via the vacuum port causes passage of liquid from the liquid source into the delivery reservoir via its inlet port and simultaneous passage of liquid from the vessel through the tube and into the disposal reservoir via its inlet port. In addition and optionally, release of the vacuum subsequent to the application of the vacuum causes passage of liquid from the delivery reservoir via its outlet port through the tube and into the vessel and simultaneous passage of liquid from the disposal reservoir via its outlet port to the waste receptacle.

The pipets of the invention can include one or more of the following optional features: The delivery and disposal reservoir are arranged side by side. The inlet port and outlet port of the delivery reservoir each includes a clack valve. The inlet port and the outlet port of the disposal reservoir each includes a clack valve. The tube is substantially rigid. The vacuum port includes a filter that blocks the passage of liquid and/or air particles into and out of the pipets. The distal end of the tube is adapted for simultaneous suction of liquid from and simultaneous delivery of liquid to a plurality of vessels (e.g., a two-dimensional array of vessels). The distal end of the tube includes a filter that blocks passage of cells while allowing liquid to flow through the tube.

The invention further includes a pipet controller having (1) a housing including an inlet port and an outlet port, the inlet port adapted to engage a pipet and the outlet port adapted for attachment to a vacuum source; (2) a conduit within the housing and connected to the inlet port and the outlet port; and (3) an adjustable valve system for controlling liquid flow through the conduit, the valve system having at least a first setting in which the vacuum source applies a vacuum to the pipet through the conduit, thereby allowing suctioning of liquid from the pipet through the conduit, and a second setting in which the vacuum source is disconnected from the conduit, thereby releasing liquid in the pipet.

The controller can have one or more of the following optional features: The valve system further has a third setting in which the vacuum source is disconnected but a homeostatic suction is maintained on the pipet the valve system includes at least one spring-loaded piston. The controller is formed of only autoclavable materials.

Also featured in the invention is a container lid having a housing defining at least a first and second passage, the first passage configured to seal a container opening having a first configuration, and the second passage configured to seal a container opening having a second configuration different from the first configuration.

The lids of the invention can have one or more of the following optional features: The first and second configurations are cylindrical but are of different diameters. The first and second passages are threaded and configured to seal a screw-top bottle. The lids further include an outlet port adapted for dispensing of liquid from the container. The outlet port is sealable. The lids further include a suction tube extending from the outlet port and into a container.

The invention also includes a pipet having (1) a delivery reservoir including an inlet port adapted for connection to a liquid source, and an outlet port including a valve that allows passage of liquid out of but not into the delivery reservoir; (2) a tube having a distal end and proximal end, the distal end adapted for suction of liquid from and delivery of liquid to a vessel, and the proximal end in communication with the outlet port of the delivery reservoir; and (4) a vacuum port contiguous with the delivery reservoir and adapted for attachment to a disposal receptacle and a vacuum source. Application of a vacuum to the pipet via the vacuum port causes passage of liquid from the liquid source into the delivery reservoir via its inlet port and simultaneous passage of liquid from the vessel through the tube, out of the vacuum port, and into the disposal receptacle.

The present pipet can be used with a mechanical pipetter widely used in laboratories, any installed vacuum source, or a pipet controller described herein. This pipet has a simple construction that can be operated easily and accurately and is versatile. Other features and advantages will be apparent from the following detailed description.

BRIEF DESCRIPTION OF THE DRAWINGS

FIGS. 2A–2C are cross-sectional views through the center of the pipet in the system shown in FIG. 1.

FIGS. 3A and 3B are cross-sectional views of alternative embodiments of the pipet shown in FIG. 1.

FIGS. 5D–5F are cross-sectional views of the container lids, cut along line A—A, as shown in FIGS. 5A–5C, respectively.

FIGS. 6A and 6B illustrate attachment devices for use in suctioning suspension cell cultures without removing cells in the culture.

DETAILED DESCRIPTION OF THE INVENTION

Figure 1:
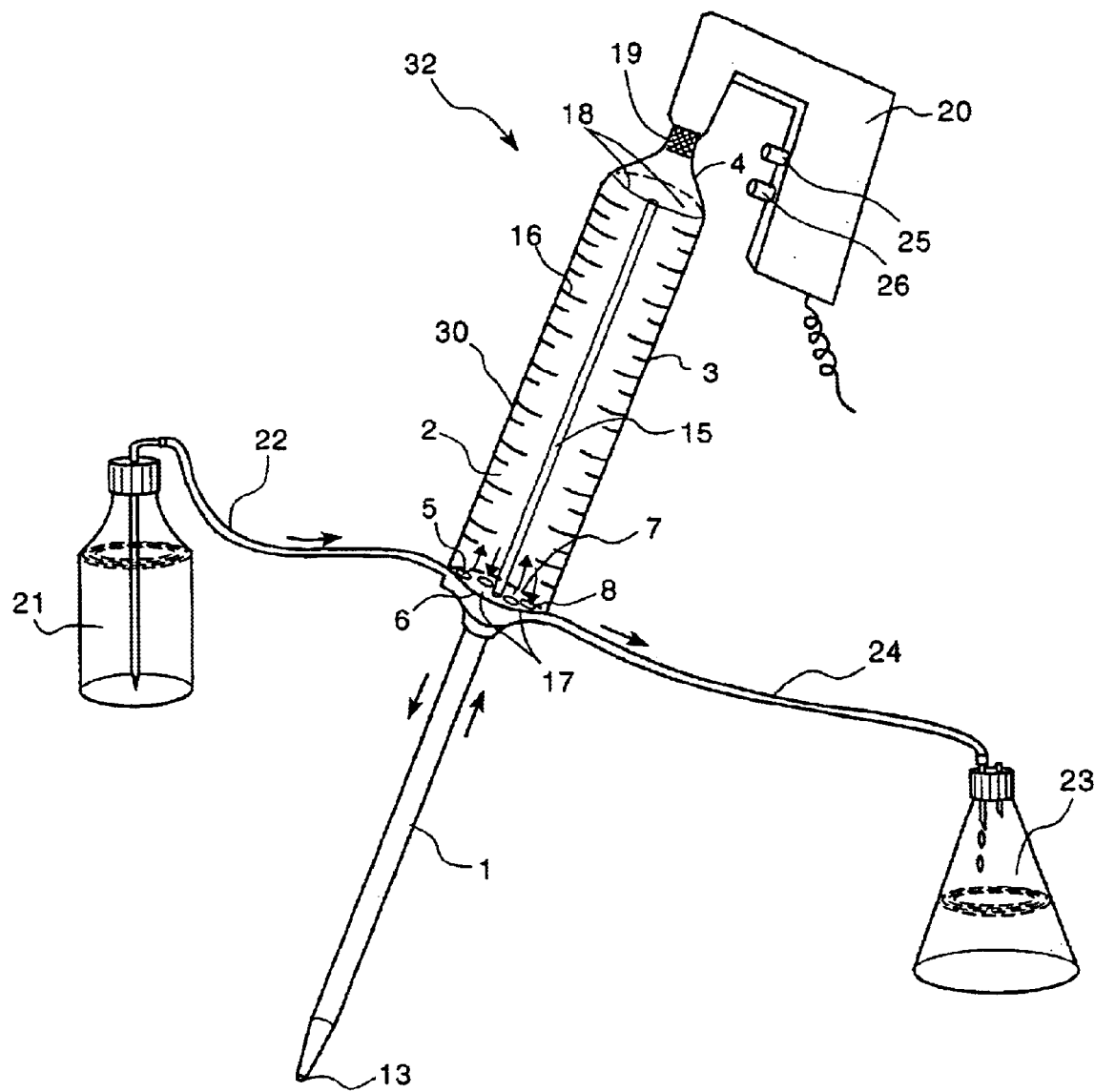
FIG. 1 is a perspective view of a pipet system of the invention.

Referring to FIGS. 1 and 2A–2C, a liquid exchange system 32 includes a pipet 30 having a tube 1, semi-circular reservoirs 2 and 3, a vacuum port 4, inlet/outlet passages 5, 6, 7, and 8, and one-way control valves 9, 10, 11, and 12. A dividing wall 15 separates reservoirs 2 and 3 from each other in pipet 30. Of course, in a separate embodiment, reservoirs 2 and 3 can be two individual cylinders coupled longitudinally, or even two reservoirs spaced apart.

Tube 1 has a distal end 13 used for drawing and delivery of liquid into and out of pipet 30 and an opening 14 (FIGS. 2A–2C) in communication with reservoirs 2 and 3 via outlet passage 6 and inlet passage 7. Graduation markings 16 on the exterior surface of pipet 30 are used for determining, by visual inspection, the volume of liquid contained in the reservoirs. The walls of pipet 30 are sufficiently transparent so that the liquid level can be seen by the user.

Each of reservoirs 2 and 3 have distal portions 17 and proximal portions 18. The proximal portions 18 of reservoirs 2 and 3 join together to form a common channel or passage, i.e., the vacuum port 4 for mounting of tube 30 onto a pipet controller 20. Vacuum port 4 includes a filter plug 19 (e.g., absorbent cotton, etc.) in its bore to block passage of particulates or liquid through the pipet. The distal portions 17 of reservoirs 2 and 3 have inlet 5 and 7 and outlet 6 and 8, respectively.

Reservoir 2 is used for temporarily storing new or replacement liquid medium, whereas reservoir 3 is used for temporarily storing the old liquid medium to be disposed. Inlet 5 of reservoir 2 is connected to a replacement liquid container 21 via a sterile tubing 22. Outlet 6 of the reservoir 2 is connected to tube 1 for draining the new medium into a culture vessel. Inlet 7 of reservoir 3 is also connected to tube 1 for drawing the old medium from the culture vessels into reservoir 3. Outlet 8 of reservoir 3 is connected to a waste collecting bottle 23 via a tubing 24. Although container 21 hold fresh medium, it is understood that any useful liquid, such as saline, can be provided in the container.

Opening or closing of each passage of the inlets 5 and 7 and outlets 6 and 8 is automatically controlled by shutter or clack valves 9, 10, 11, and 12. The valves serve as one-way controllers that open or close in response to pressure differences inside reservoirs 2 and 3. Indeed, any valve can be used, so long as the valve is formed of a non-toxic material, is stable in liquid and air, and provides one-way closure.

The pressure state (either vacuum or high pressure) is provided by pipet controller 20. As shown in FIG. 2B, when vacuum is applied to reservoirs 2 and 3, valves 9, 10, 11, and 12 move upward to open inlets 5 and 7 and close outlets 6 and 8, thereby drawing new medium into reservoir 2 and old medium into reservoir 3 via inlet 5 and the inlet 7, respectively. Conversely, as shown in FIG. 2C, when the vacuum is eliminated and a high (or positive) atmospheric pressure is applied, valves 9, 10, 11, and 12 move downward to open outlets 6 and 8 and close inlets 5 and 7. Now the new medium and the old medium are simultaneously drained from reservoir 2 and reservoir 3 via outlet 6 and outlet 8 into culture vessel (not shown) and disposal receptacle 23, respectively. However, other mechanisms for accomplishing the same result can be envisioned by those skilled in the art and consequently are considered a part of this invention as well.

System 32 can be used as follows.

1) Hold pipet controller 20 with one hand and immerse tip 13 of tube 1 into the old liquid medium to be disposed.

2) Press a button 25 on pipet controller 20 to apply vacuum to reservoirs 2 and 3, thereby drawing the new medium and the old medium simultaneously into reservoir 2 and reservoir 3 via inlet 5 and inlet 7, respectively.

3) Release button 25 (now the fluid flow stops) and press another control button 26 of pipet controller 20 to apply a high (or positive) atmospheric pressure to reservoirs 2 and 3, thereby expelling or discharging the new medium and the old medium simultaneously from reservoir 2 and reservoir 3 via outlet 6 and outlet 8 into culture vessel and disposal receptacle 23, respectively.

Thus, the operator can accomplish the task of changing liquid medium in one single step without the need for changing pipets. In addition, the pipet of the present invention can be used solely for aspiration of a liquid for disposal or solely for addition or dispensation of a liquid.

Other options which may be desirable include a second tube 27 (FIG. 3A) connected to outlet 6 and in parallel with first tube 1 (which is connected to inlet 7) but shorter. This separation of the passages for outlet 6 and inlet 7 helps eliminate cross-contamination as pipet 30 is moved from one vessel to another.

In another embodiment, a manifold 28 (FIG. 3B) with different number of ports spaced to fit the wells of a microplate can be attached to tip 13 of the tube 1. Manifold 28 is useful for changing medium in multiple-well microplates (e.g., 96 well plate).

Figure 4A:
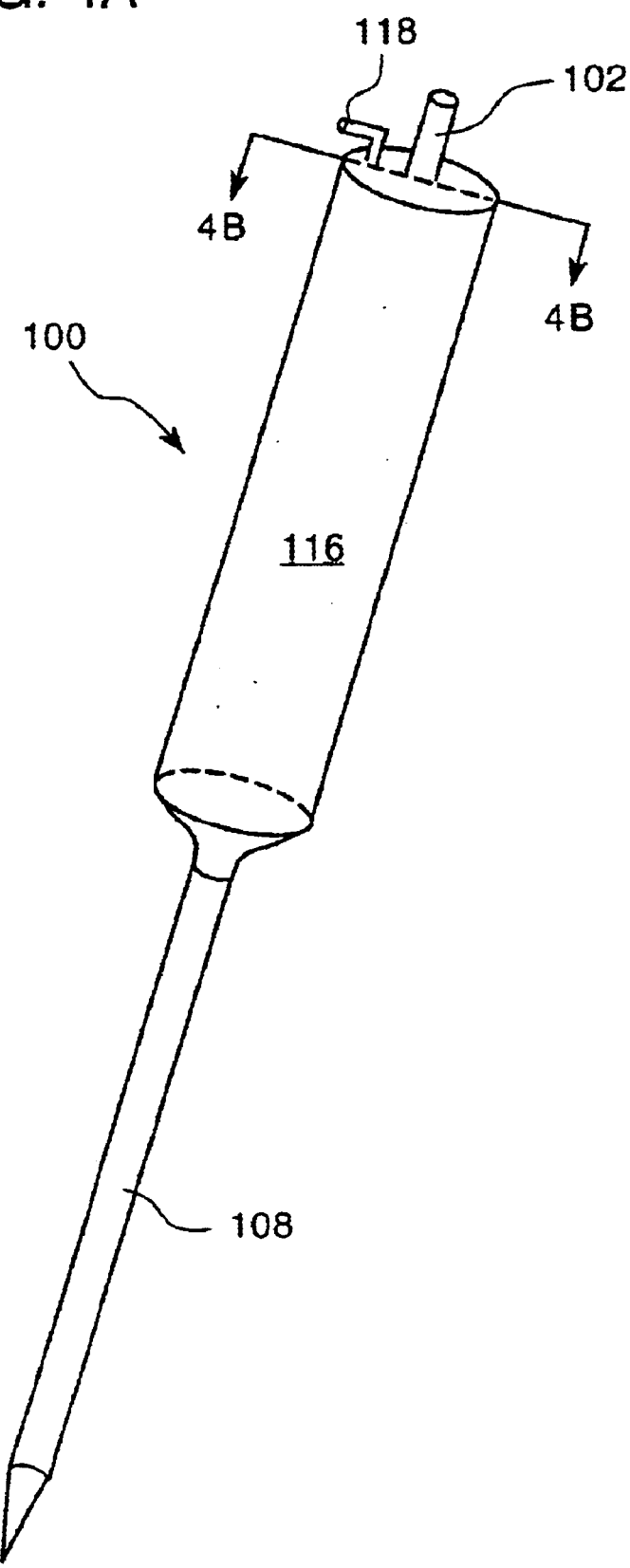
FIG. 4A is a perspective view of a pipet of the invention.
Figure 4B:
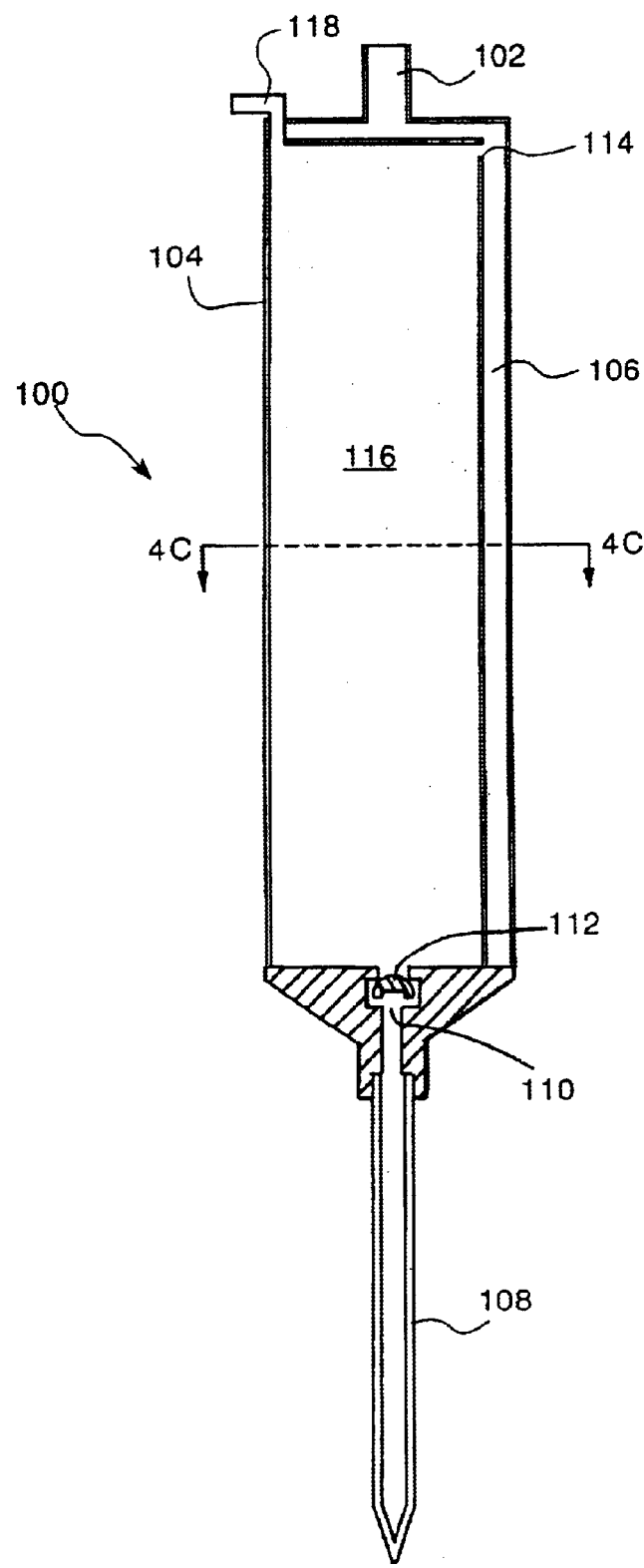
FIG. 4B is a vertical cross-section along the length of the pipet at line A—A shown in FIG. 4A.
Figure 4C:
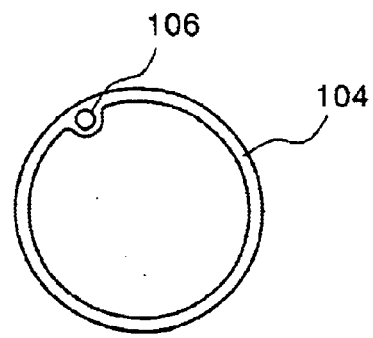
FIG. 4C is a horizontal cross-section of the pipet along line B—B shown in FIG. 4B.

Referring to FIGS. 4A–4C, a liquid exchange system includes an alternative form of a pipet 100. Pipet 100 includes a mounting tube 102 for coupling to a vacuum source and waste receptacle. Mounting tube 102 is in communication with a reservoir 116, which is formed by housing 104, via an opening 114 in a passage 106 embedded in wall of housing 104. A tube 108 is in communication with reservoir 116 via an outlet 110, passage of liquid through which is controlled by clack valve 112. Alternative valves suitable for use in the pipets of the invention (e.g., shutter valves) are know to one skilled in the art. Medium or liquid enters reservoir 116 through inlet 118, which during operation is connected to a source of liquid.

In actual use, pipet 100 operates similarly to pipet 30 shown in FIG. 1, except that the waste liquid is not held in a reservoir within pipet 100. In other words, when vacuum is applied to pipet 100 via vacuum port 102, liquid is immediately suctioned into member 108, through passage 106 and port 102 and into a waste receptacle (not shown). Simultaneously, the vacuum is also applied to reservoir 116 via opening 114, resulting in the introduction of fresh medium from a liquid source (not shown) into reservoir 116 via inlet 118. When vacuum pressure ceases and vacuum port 102 is exposed to ambient air, fresh medium flows through outlet 110 into member 108 and out of pipet 100.

Figure 5A:
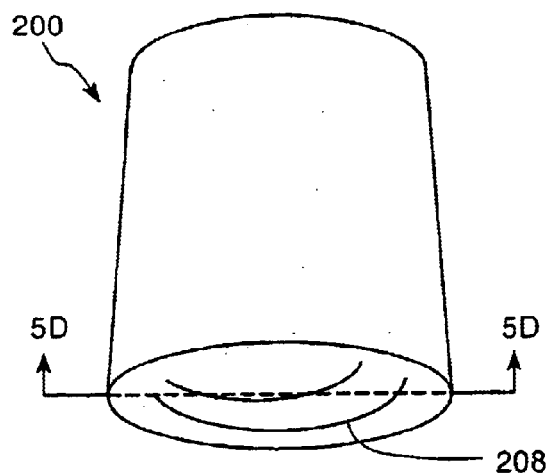
FIGS. 5A–5C are perspective views of container lids of the invention.

Referring back to FIG. 1 and replacement liquid container 21, it is understood that tissue culture medium is often purchased in bottles with standard screw-top caps. Thus, an additional feature of the invention is a multi-size screw top cap adapted to fit and seal two or more standardized bottle sizes. A dual-size screw top cap is shown in FIGS. 5A and 5D. Cap 200 is formed of housing 202, which defines a large-diameter cylindrical threaded passage 204 having threads 208 and a smaller diameter cylindrical passage 206 having threads 210. In the case of tissue culture medium bottles, passage 204 can have a diameter of about 3.8 cm, and passage 206 can have a diameter of about 3.0 cm, both diameters corresponding to standard tissue culture medium bottles. Thus, the single cap 200 can be used to seal bottles have mouths of different sizes. Of course, instead of threads, the passages can be configured to seal a container opening using any other mechanisms or configurations, including a detent mechanism.

For the replacement liquid container 21 shown in FIG. 1 to be useful in system 32, the bottle cap must contain an outlet for the medium. In the configuration shown in FIGS. 5B and 5E, bottle cap 300 includes a housing 302 defining a cylindrical passage 304 having threads 316 that are adapted to couple with a mouth of a bottle containing medium. Cap 300 also includes outlet port 306, which has an exterior portion 308 and an interior portion 310. Outlet port 306 includes a removable cover 314 for capping an opening 316 in exterior portion 308. Cover 314 is attached to a portion of outlet port 306 by tether 318. During operation within system 32, interior portion 310 is coupled to a tubing 312, which is immersed in the medium to be transferred, and cover 314 is removed so that, e.g., tubing 22 in system 32 of FIG. 1 can be connected to outlet port 306. Although exterior portion 308 is bent 90° relative to interior portion 310 so that the tube leading from the exterior portion 308 can be positioned away from the user's moving hands, it is understood that other configurations for outlet port 306 are suitable for use in the invention.

Figure 5B:
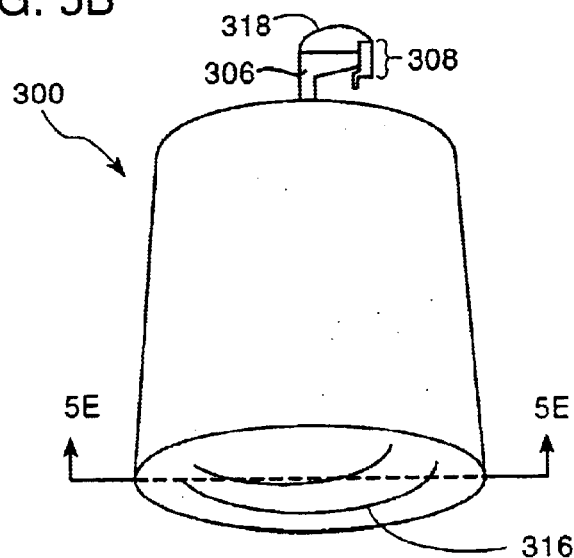
Figure 5C:
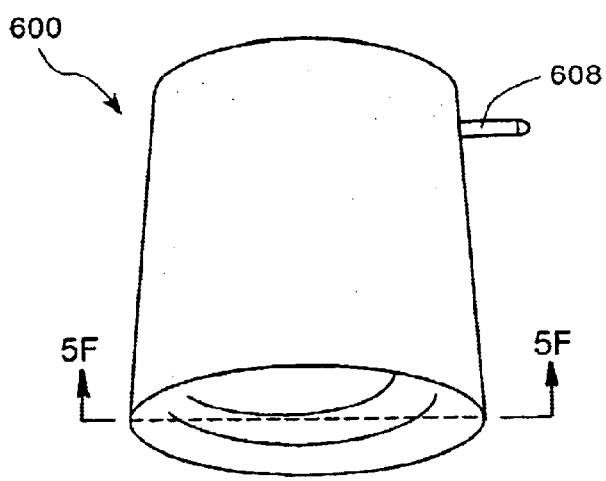
Figure 5D:
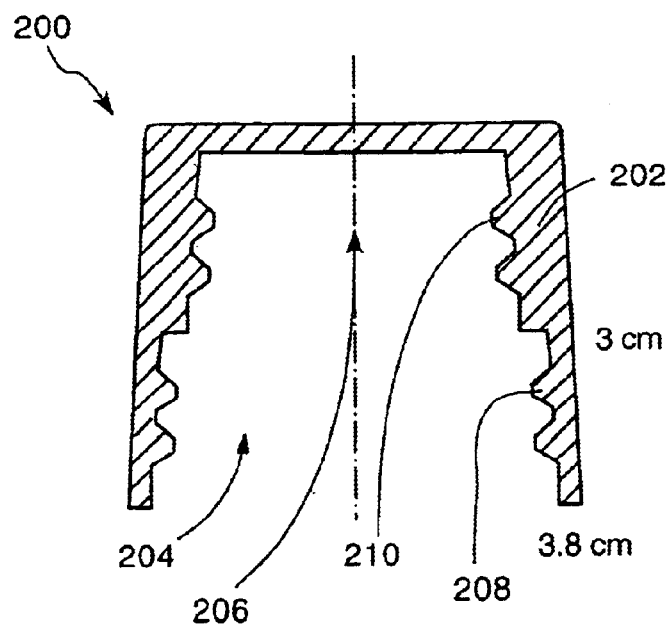
Figure 5E:
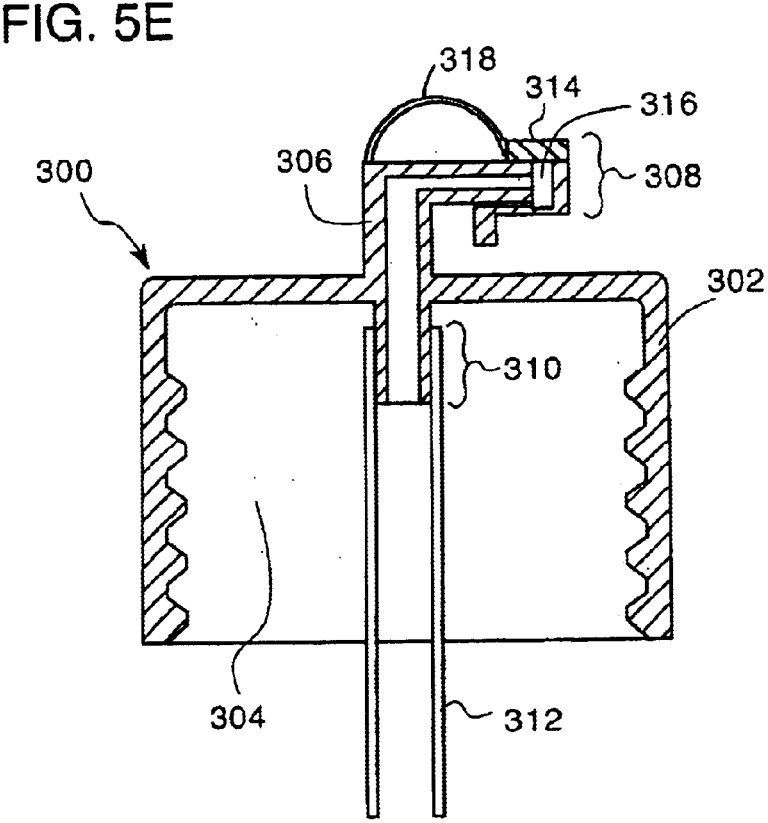

For example, the features of the dual-size screw top cap shown in FIGS. 5A and 5D can be combined with the outlet port arrangement shown in FIGS. 5B and 5E to provide a cap 600 as shown in FIGS. 5C and 5F. Cap 600 is formed of a housing 602 that defines a larger diameter cylindrical, threaded passage 604 and a smaller diameter cylindrical, threaded passage 606. Cap 600 also includes outlet port 608, which is embedded in housing 602 and does not extend from the top of the cap, as is shown for cap 300 in FIG. 5B. Instead, outlet port 608 emerges from the side of cap 600.

Another feature of the invention is an attachment, e.g., for distal tip 13 of tube 1 of pipet 30 (FIG. 1), that allows suction of suspension cell cultures without removing the cells in the culture. This is desirable when the number of cells in culture should be maximized. Two embodiments of such an attachment are shown in FIGS. 6A and 6B. In FIG. 6A, attachment 400 includes a neck 402 adapted to be removably coupled to tip 13 of tube 1 (FIG. 1) and conical section 404 having mouth 406. Attachment 400 has a grate 408 covering mouth 406 and supporting a membrane 410. Membrane 410 contains pores of a size that allows suction of medium but not cells through attachment 400.

To increase the surface area through which old media can be suctioned and to minimize the clogging of the membrane by cells, another embodiment of an attachment is shown in FIG. 6B. Attachment 500 includes neck 502 adapted to be removably coupled to tip 13 of tube 1 (FIG. 1), a support scaffold 504, and a membrane 506 having pores of a size that allows suction of medium but not cells through attachment 500.

It is noted that attachments need not be used when feeding suspension cell cultures, especially when loss of cells is not a problem. In addition, the attachment can be formed of inexpensive materials so that a user can discard the attachment after a first use, or formed of relatively strong materials that can survive sterilization techniques, such as autoclaving. In addition, the attachments can be integrated with tube 1 to form a single non-removable piece.

Figure 7A:
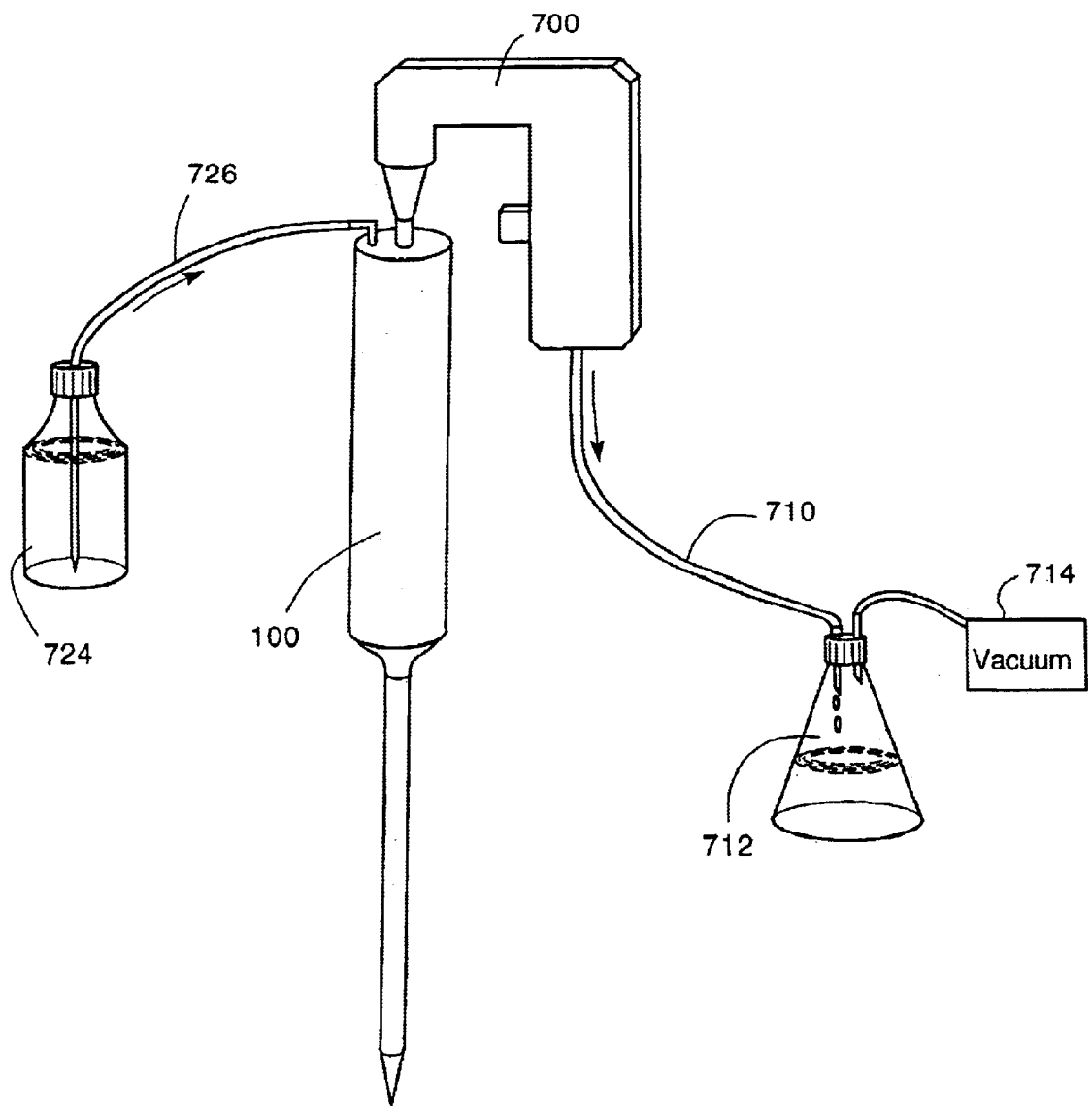
FIG. 7A is a perspective view of a pipet system, including a pipet controller of the invention.
Figure 7B:
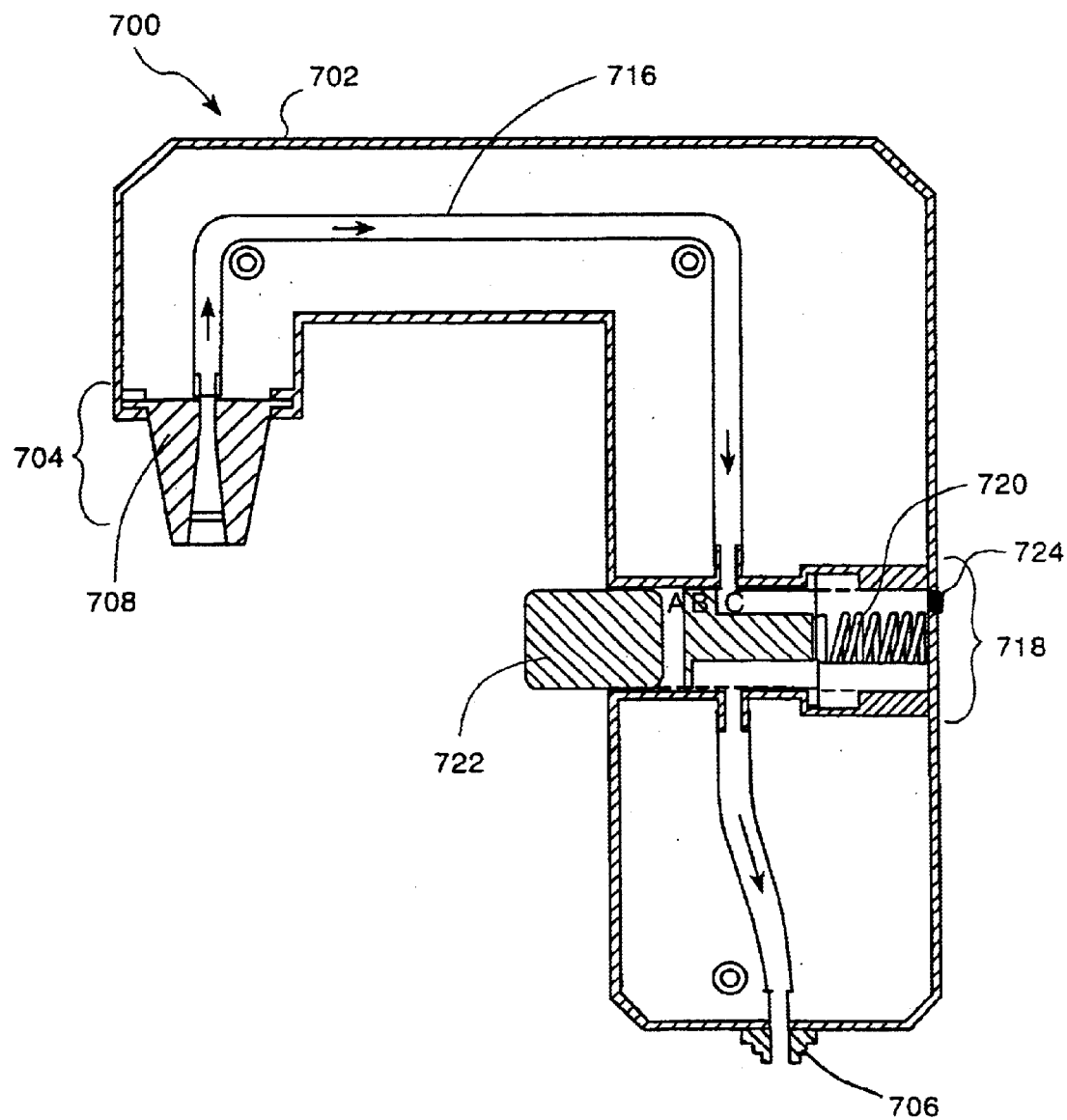
FIG. 7B is a cross-sectional view of the pipet controller shown in FIG. 7A.
Figure 7C:
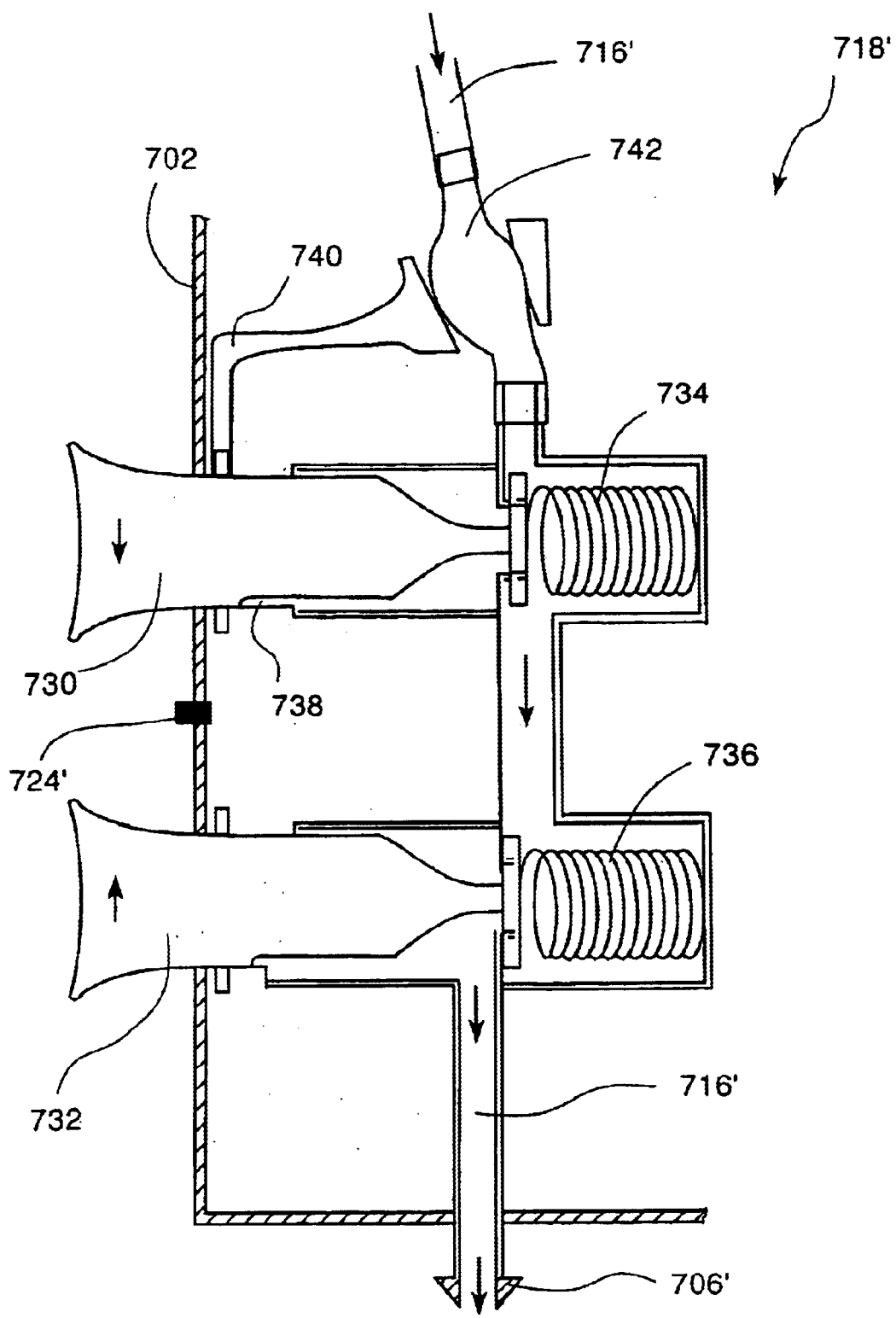
FIG. 7C is a cross-sectional view of a portion of a pipet controller having an alternative valve system.

The pipet controllers of the invention differ from previously available pipet controllers because the present controllers allows liquid flow through the controller, while previous controllers are designed to specifically block passage of liquid into the controller. Referring to FIGS. 7A–7C, the invention includes a pipet controller 700 that can be used with pipet 100 shown in FIGS. 4A–4C. Controller 700 is formed of housing 702, which is shaped for hand operation. Housing 702 includes an inlet port 704 and an outlet port 706. Inlet port 704 includes a rubber stopper 708 designed to accommodate and seal around a vacuum port of a pipet (e.g., vacuum port 102 of pipet 100 shown in FIGS. 4A–4C). Outlet port 706 is adapted to fit a standard vacuum tubing 710, leading to a waste receptacle 710 and vacuum source 714 (e.g., a standard house vacuum line often found in laboratories).

A conduit 716 within housing 702 links inlet port 704 and outlet port 706. Connected to conduit 716 is a valve system 718, which includes a spring 720 and a piston 722. The position of piston 722 is biased by spring 720. In normal operation the user's fingers depresses piston 722 to position A, thereby applying a vacuum to conduit 716 and pipet 100. Liquid is then suctioned from a vessel using tube 108 of pipet 100. This disgarded liquid travels through housing 702 via conduit 716, out through vacuum tubing 710 and into waste receptacle 712. Simultaneously, liquid flows from container 724, through tubing 726, and into pipet 100 as described above. The user can then temporarily hold liquid in reservoir 116 of pipet 100 by allowing piston 722 to move to position B, where the pressure in conduit 716, and consequently in pipet 100, is homeostatic. The user then fully releases piston 722 to rest in position C, where conduit 716 is exposed to the ambient atmosphere through hole 724 in housing 702. Accordingly, liquid flows from pipet 100 into a vessel via tube 108.

FIG. 7C shows an alternative valve system 718' that can be used in place of valve system 718 described above. In this embodiment, valve system 718' includes pistons 730 and 732, each of which are biased by springs 734 and 736, respectively. In typical operation using valve system 718', piston 732 is depressed to connect conduit 716' with a vacuum source via outlet port 706'. Accordingly, liquid flows from pipet 100, through conduit 716' and out of the controller through outlet port 706'. Next, the user can temporarily pause the operation by releasing piston 732 to its resting position, thereby applying homeostatic pressure to pipet 100. To release liquid from pipet 100, piston 730 is depressed exposing conduit 716' to ambient atmosphere through hole 724' in housing 702'. To accomplish this release, piston 730 contains a passage 738 along one side. When piston 730 is depressed, passage 738 is in communication with both conduit 716' and hole 724'.

Piston 730 also includes a lever arm 740. When piston 730 is depressed to release liquid in pipet 100, lever arm 740 presses a bulb 742 integrated into conduit 716' to expel a final volume of air into pipet 100. This final volume of air aides delivery of the very last amount of liquid in tube 108 of pipet 100 to a vessel.

The liquid exchange systems described above can also be used in conjunction with robotic or automated pipetting systems that employ pipets as described above. For example, manifold 28 shown in FIG. 3B can contain multiple ports in one dimension (FIG. 3B) or two dimensions, such as a 8×12-port configuration corresponding to a standard 96-well microplate. In addition, pipet 30 can be mounted onto an addressable carrier and can position a manifold anywhere within two or three dimensions. Although in the above configuration one pipet is connected to 96 ports, it is understood that the port:pipet ratio can range from 1:1 to greater than 96:1 by miniaturizing the various components and mounting the components on an addressable robotic arm. Robotic machines that can be adapted for use in such an addressable, high throughput pipetting system include automated microplate pipetting and washer systems available from Bio-Tek, Inc.; Plate Track, Inc.; and Packard Instruments, Inc.

The pipets, systems, pipet controllers, or accessories described herein can be formed of materials that can be easily sterilized, e.g., by autoclaving. However, if sterilization is not a consideration, then more advanced but more fragile components can be used. For example, the valves, ports, actuators, and other controls can be electromechanical and contain electronic circuits.

While the invention has been described and illustrated with reference to specific embodiments, it is understood that other embodiments may be resorted to without departing from the invention. Therefore the form of the invention set out above should be considered only illustrative and not limiting. Additional embodiments of the invention are included in the claims below.

What is claimed is:

1. A pipet comprising
   a delivery reservoir including
      an inlet port that allows passage of liquid into but not out of the delivery reservoir, the inlet port adapted for attachment to a liquid source, and
      an outlet port that allows passage of liquid out of but not into the delivery reservoir, the delivery reservoir formed of a material substantially transparent to allow visual inspection of liquid level within the delivery reservoir;
   a disposal reservoir including
      an inlet port that allows passage of liquid into but not out of the disposal reservoir, and
      an outlet port that allows passage of liquid out of but not into the disposal reservoir, the outlet port adapted for attachment to a waste receptacle, and the disposal reservoir formed of a material substantially transparent to allow visual inspection of liquid level within the disposal reservoir;
   a tube having a distal end and proximal end, the distal end adapted for suction of liquid from and delivery of liquid to a vessel, and the proximal end in communication with the outlet port of the delivery reservoir and the inlet port of the disposal reservoir; and
   a vacuum port contiguous with the delivery reservoir and the disposal reservoir and adapted for attachment to a vacuum source,
   wherein application of a vacuum to the pipet via the vacuum port causes passage of liquid from the liquid source into the delivery reservoir via its inlet port and simultaneous passage of liquid from the vessel through the tube and into the disposal reservoir via its inlet port.

2. The pipet of claim 1, wherein release of the vacuum subsequent to the application of the vacuum causes passage of liquid from the delivery reservoir via its outlet port through the tube and into the vessel and simultaneous passage of liquid from the disposal reservoir via its outlet port to the waste receptacle.

3. The pipet of claim 1, wherein the delivery and disposal reservoir are arranged side by side.

4. The pipet of claim 1, wherein the inlet port and outlet port of the delivery reservoir each comprises a clack valve.

5. The pipet of claim 1, wherein the inlet port and the outlet port of the disposal reservoir each comprises a clack valve.

6. The pipet of claim 1, wherein the tube is substantially rigid.

7. The pipet of claim 1, wherein the vacuum port includes a filter that blocks the passage of liquid or solid particles out of the pipet.

8. The pipet of claim 1, wherein the distal end of the tube is adapted for simultaneous suction of liquid from and simultaneous delivery of liquid to a plurality of vessels.

9. The pipet of claim 8, wherein the plurality of vessels is a two-dimensional array of vessels.

10. The pipet of claim 1, wherein the distal end of the tube includes a filter that blocks passage of cells while allowing liquid to flow through the tube.

11. A pipet comprising
   a delivery reservoir including
      an inlet port that allows passage of liquid into but not out of the delivery reservoir, the inlet port adapted for attachment to a liquid source, and
      an outlet port that allows passage of liquid out of but not into the delivery reservoir, the delivery reservoir formed of a material substantially transparent to allow visual inspection of liquid level within the delivery reservoir;
   a disposal reservoir including
      an inlet port that allows passage of liquid into but not out of the disposal reservoir, and
      an outlet port that allows passage of liquid out of but not into the disposal reservoir, the outlet port adapted for attachment to a waste receptacle, and the disposal reservoir formed of a material substantially transparent to allow visual inspection of liquid level within the disposal reservoir;
   a suction tube having a distal end adapted for suction of liquid from a vessel and a proximal end in communication with the inlet port of the disposal reservoir;
   a delivery tube having a distal end adapted for delivery of liquid from a vessel and a proximal end in communication with the outlet port of the delivery reservoir; and
   a vacuum port contiguous with the delivery reservoir and the disposal reservoir and adapted for attachment to a vacuum source,
   wherein application of a vacuum to the pipet via the vacuum port causes passage of liquid from the liquid source into the delivery reservoir via its inlet port and simultaneous passage of liquid from the vessel through the delivery tube and into the disposal reservoir via its inlet port.

12. The pipet of claim 11, wherein release of the vacuum subsequent to application of the vacuum causes passage of liquid from the delivery reservoir via its outlet port through the delivery tube and into the vessel and simultaneous passage of liquid from the disposal reservoir via its outlet port to the waste receptacle.

13. A pipet comprising
   a first means for holding liquid to be delivered into a vessel, the first means including
      a second means for allowing passage of liquid into but not out of the first means, the second means adapted for attachment to a liquid source, and
      a third means for allowing passage of liquid out of but not into the first means, the first means formed of a material substantially transparent to allow visual inspection of liquid level within the first means;
   a fourth means for holding liquid to be disgarded, the fourth means including
      a fifth means for allowing passage of liquid into but not out of the fourth means;
      a sixth means for allowing passage of liquid out of but not into the fourth means, the sixth means adapted for attachment to a waste receptacle, and the fourth means formed of a material substantially transparent to allow visual inspection of liquid level within the fourth means;
   a seventh means for suction of liquid from and delivery of liquid to a vessel, the seventh means being in communication with the third means and the fifth means; and
   a eighth means contiguous with the first means and the fourth means, the eighth means adapted for attachment to a vacuum source,
   wherein application of a vacuum to the pipet via the eighth means causes passage of liquid from the liquid source into the first means via the second means and simultaneous passage of liquid from the vessel through the seventh means and into the fourth means via the fifth means.

14. A pipet comprising
   a delivery reservoir including
      an inlet port adapted for connection to a liquid source, and
      an outlet port comprising a valve that allows passage of liquid out of but not into the delivery reservoir;
   a tube having a distal end and proximal end, the distal end adapted for suction of liquid from and delivery of liquid to a vessel, and the proximal end in communication with the outlet port of the delivery reservoir; and
   a vacuum port contiguous with the delivery reservoir and adapted for attachment to a disposal receptacle and a vacuum source,
   wherein application of a vacuum to the pipet via the vacuum port causes passage of liquid from the liquid source into the delivery reservoir via its inlet port and simultaneous passage of liquid from the vessel through the tube, out of the vacuum port, and into the disposal receptacle.

* * * * *